United States Patent [19]

Mapelli et al.

[11] Patent Number: 5,516,642
[45] Date of Patent: May 14, 1996

[54] POLYPEPTIDES DERIVED FROM MAJOR HISTOCOMPATIBILITY COMPLEX CLASS I ANTIGEN

[75] Inventors: Claudio Mapelli, Plainsboro; Chester A. Meyers, Medford, both of N.J.

[73] Assignee: Bristol-Myers Squibb Company, Princeton, N.J.

[21] Appl. No.: 976,872

[22] Filed: Nov. 16, 1992

[51] Int. Cl.⁶ .............................. C07K 7/08; C07K 14/00; G01N 33/534
[52] U.S. Cl. .................... 435/7.21; 424/1.69; 435/7.8; 530/324; 530/325; 530/326; 530/327
[58] Field of Search ................... 435/7.21, 7.8; 530/303, 326, 327, 324–325; 424/1.69

[56] References Cited

U.S. PATENT DOCUMENTS 5,073,540  12/1991  Olsson ............................ 514/3

OTHER PUBLICATIONS

S. Buus et al, *Science*, 235, 1353–1358, 1987.
K. L. Constantine et al, *Jour. Biol. Chem.*, 268, 22830–22837, 1993.
A. Sette et al, *Nature*, 328, 395–399, 1987.
J. Stagsted et al, *Proc. Natl. Acad. Sci. USA*, 90, 7686–7690, 1993.
N–S Liao et al., Science, vol. 253, pp. 199–202, Jul. 1991.
M. J. Grusby et al., Science, vol. 253, pp. 1417–1420, Sep. 1991.
M. Bix et al., Nature, vol. 349, pp. 329–331, Jan. 1991.
M. Zijlstra et al., Nature, vol. 344, pp. 742–746, Apr. 1990.
J. Stagsted et al., Cell, vol. 62, pp. 297–307, Jul. 27, 1990.
J. Stagsted et al., The Journal of Biological Chemistry, vol. 266, No. 20, pp. 12844–12847, Issue of Jul., 1991.

*Primary Examiner*—David Saunders
*Attorney, Agent, or Firm*—Timothy J. Gaul

[57] ABSTRACT

Disclosed herein are polypeptides of the formula $$R^1-AA-A^1-A^2-A^3-A^4-A^5-A^6-A^7-A^8-A^9-A^{10}-A^{11}-A^{12}-A^{13}-R^2$$

that are useful in treatment of diabetes mellitus, wherein:

AA is a single bond or a polypeptide chain of 1 to 12 natural amino acid residues;

$A^1$ is seryl, $A^2$ is phenylalanyl, $A^3$ is arginyl, $A^4$ is valyl, $A^5$ is aspartyl, $A^6$ is leucyl, $A^7$ is arginyl, $A^8$ is threonyl, $A^9$ is leucyl, $A^{10}$ is leucyl, $A^{11}$ is arginyl, and $A^{12}$ is tyrosyl, wherein one of $A^1$ through $A^{12}$ may be replaced with a natural amino acid residue, and wherein when $A^{12}$ is phenylalanyl, tyrosyl or tryptophyl, its aromatic ring may be substituted with 1 or 2 iodo atoms;

$A^{13}$ is a natural amino acid residue other than tyrosyl, the D-form of a natural amino acid residue, $-N(R^4)-CH(R^3)-C(O)-$, or $-N(R^4)-CH(R^3)-CH_2-$;

$R^1$ is hydrogen, lower alkyl, $R^5-C(O)-$, aryl, aryl(lower alkyl), cycloalkyl, cycloalkyl(lower alkyl), aryl(lower alkoxy), cycloalkyl(lower alkoxy), or arylsulfenyl, wherein the aryl or cycloalkyl may be substituted with 1 to 5 substituents selected from 1 to 5 halo, 1 to 3 nitro, 1 to 5 lower alkyl, and 1 to 5 lower alkoxy groups;

$R^2$ is hydrogen, lower alkyl, aryl, aryl(lower alkyl), cycloalkyl, cycloalkyl(lower alkyl), hydroxyl, lower alkoxy, aryloxy, aryl(lower alkoxy), cycloalkyloxy, cycloalkyl(lower alkoxy), $N_3$, $-NR^6R^7$, or $-N(R^8)-NR^6R^7$;

$R^3$ is hydrogen, $-R^9-R^{10}$, or $-NR^6R^7$, and $R^4$ is hydrogen or alkyl, or $R^3$ and $R^4$ together are alkylene;

and the remaining symbols are as defined in the specification.

13 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Gly  Asn  Glu  Gln  Ser  Phe  Arg  Val  Asp  Leu  Arg  Thr  Leu  Leu  Arg  Tyr
 1                  5                        10                            15
Ala
```

( 2 ) INFORMATION FOR SEQ ID NO:2:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear (  i i  ) MOLECULE TYPE: peptide (  i x  ) FEATURE:
    ( A ) NAME/KEY: Modified-site
    ( B ) LOCATION: 3
    ( D ) OTHER INFORMATION: /label=sidechain
        / note="O-(1,1-dimethylethyl)"

(  i x  ) FEATURE:
    ( A ) NAME/KEY: Modified-site
    ( B ) LOCATION: 5
    ( D ) OTHER INFORMATION: /label=sidechain
        / note="S-(1,1-dimethylethyl)"

(  i x  ) FEATURE:
    ( A ) NAME/KEY: Modified-site
    ( B ) LOCATION: 7
    ( D ) OTHER INFORMATION: /label=sidechain
        / note="N-(PMC)"

(  i x  ) FEATURE:
    ( A ) NAME/KEY: Modified-site
    ( B ) LOCATION: 9
    ( D ) OTHER INFORMATION: /label=sidechain
        / note="O-(1,1-dimethylethyl)"

(  i x  ) FEATURE:
    ( A ) NAME/KEY: Modified-site
    ( B ) LOCATION: 11
    ( D ) OTHER INFORMATION: /label=sidechain
        / note="N-(PMC)"

(  i x  ) FEATURE:
    ( A ) NAME/KEY: Modified-site
    ( B ) LOCATION: 12
    ( D ) OTHER INFORMATION: /label=sidechain
        / note="O-[(1,1-dimethylethyl)carbonyl]"

(  i x  ) FEATURE:
    ( A ) NAME/KEY: Modified-site
    ( B ) LOCATION: 15
    ( D ) OTHER INFORMATION: /label=sidechain
        / note="N-(PMC)"

(  i x  ) FEATURE:
    ( A ) NAME/KEY: Modified-site
    ( B ) LOCATION: 16
    ( D ) OTHER INFORMATION: /label=sidechain
        / note="O-(1,1-dimethylethyl)"

(  i x  ) FEATURE:
    ( A ) NAME/KEY: Modified-site
    ( B ) LOCATION: 17
    ( D ) OTHER INFORMATION: /label=ester
        / note="[4-[(4-resinphenyl)methoxy]phenyl]methyl
        ester at C- terminus"

(  x i  ) SEQUENCE DESCRIPTION: SEQ ID NO:2:

Gly Asn Glu Gln Ser Phe Arg Val Asp Leu Arg Thr Leu Leu Arg Tyr
1               5                   10                  15

Ala ( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide (  i x  ) FEATURE:
        ( A ) NAME/KEY: Modified-site
        ( B ) LOCATION: 16
        ( D ) OTHER INFORMATION: /label=sidechain / note="4-hydroxy-3-iodo"

( x i ) SEQUENCE DESCRIPTION: SEQ ID NO:3:

Gly Asn Glu Gln Ser Phe Arg Val Asp Leu Arg Thr Leu Leu Arg Phe
1               5                   10                  15

Ala ( 2 ) INFORMATION FOR SEQ ID NO:4:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 16
    ( D ) OTHER INFORMATION: /label=sidechain
        / note="4-hydroxy-3,5-diiodo"

( x i ) SEQUENCE DESCRIPTION: SEQ ID NO:4:

Gly Asn Glu Gln Ser Phe Arg Val Asp Leu Arg Thr Leu Leu Arg Phe
1               5                   10                  15

Ala

POLYPEPTIDES DERIVED FROM MAJOR HISTOCOMPATIBILITY COMPLEX CLASS I ANTIGEN

FIELD OF THE INVENTION

The present invention concerns peptides derived from the major histocompatibility complex (MHC) Class I antigens and uses thereof.

BACKGROUND OF THE INVENTION

Polypeptides derived from the MHC Class I antigens have been found to increase glucose uptake in mammalian adipocytes above that obtained with maximal insulin stimulation. See U.S. Pat. No. 5,073,540, issued Dec. 17, 1991; Stagsted et al., Cell 62, 297–307 (1990). Such polypeptides have also been shown to prolong the effect of insulin and to inhibit insulin-induced internalization of the insulin receptor. These findings suggest a role for such polypeptides in the treatment of diseases such as diabetes mellitus.

The MHC Class I-derived polypeptides that are known to date, however, have several drawbacks that impede their utility. These drawbacks include low potency, instability in biological assay buffers, loss of activity after radioiodination, and gel formation. Stagsted et al., *J. Biol. Chem.*, 266, 12844–12847 (1991 ). A need exists, therefore, for MHC Class I-derived polypeptides that maintain the desireable properties, such as increased glucose uptake, and avoid the undesireable properties, such as instability in bioassay buffers and gel formation.

To date, a tyrosyl residue at the carboxyl terminus was considered critical for the biological activity of MHC Class I-derived polypeptides. Stagsted et al., *Cell*, 62, at 302.

BRIEF DESCRIPTION OF THE INVENTION

In accordance with the present invention, polypeptides of the formula I
$R^1$—AA—$A^1$—$A^2$—$A^3$—$A^4$—$A^5$—$A^6$—$A^7$—$A^8$—$A^9$—$A^{10}$—$A^{11}$—$A^{12}$—$A^{13}$—$R^2$ enhance glucose transport and are thus useful in screening for compounds with a similar mode of action or in the direct treatment of diabetes mellitus. In the foregoing formula and throughout this specification, the symbols am defined as follows:
AA is a single bond or a: polypeptide chain of 1 to 12 natural amino acid residues;
$A^1$ is seryl;
$A^2$ is phenylalanyl;
$A^3$ is arginyl;
$A^4$ is valyl;
$A^5$ is aspartyl;
$A^6$ is leucyl;
$A^7$ is arginyl;
$A^8$ is threonyl;
$A^9$ is leucyl;
$A^{10}$ is leucyl;
$A^{11}$ is arginyl; and
$A^{12}$ is tyrosyl;
wherein one of $A^1$ through $A^{12}$ may be replaced with a natural amino acid residue;
wherein when $A^{12}$ is phenylalanyl, tyrosyl or tryptophyl, its aromatic ring may be substituted with 1 or 2 iodo atoms;
$A^{13}$ is a natural amino acid residue other than tyrosyl, the D-form of a natural amino acid residue,

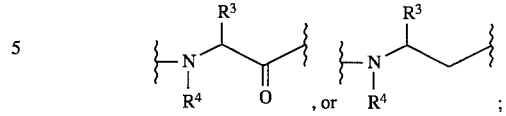

$R^1$ is hydrogen, lower alkyl, $R^5$—C(O)—, aryl, aryl(lower alkyl), cycloalkyl, cycloalkyl(lower alkyl), aryl(lower alkoxy), cycloalkyl(lower alkoxy), or arylsulfenyl, wherein the awl or cycloalkyl may be substituted with 1 to 5 substituents selected from I to 5 halo, 1 to 3 nitro, 1 to 5 lower alkyl, and 1 to 5 lower alkoxy groups; $R^2$ is hydrogen, lower alkyl, aryl, aryl(lower alkyl), cycloalkyl, cycloalkyl(lower alkyl), hydroxyl, lower alkoxy, aryloxy, aryl(lower alkoxy), cycloalkyloxy, cycloalkyl(lower alkoxy), $N_3$,

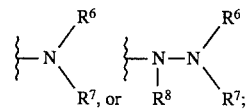

$R^3$ is hydrogen, —$R^9$—$R^{10}$, or

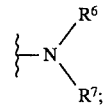

$R^4$ is hydrogen or alkyl, or $R^3$ and $R^4$ together are alkylene;
$R^5$ is lower alkyl, aryl, aryl(lower alkyl), cycloalkyl, cycloalkyl(lower alkyl), lower alkoxy, aryloxy, aryl(lower alkoxy), cycloalkyl(lower alkoxy), fluorenyl(lower alkoxy),

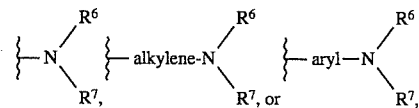

wherein the awl or cycloalkyl groups may be substituted with 1 to 5 substituents selected from 1 to 5 halo, 1 to 3 nitro, 1 to 5 lower alkyl, and 1 to 5 lower alkoxy groups;
$R^6$, $R^7$ and $R^8$ are each independently hydrogen, alkyl, aryl, cycloalkyl, aralkyl, or cycloalkylalkyl, or any two of $R^6$, $R^7$ and $R^8$ together are alkylene or alkenylene;
$R^9$ is a single bond, alkyl, alkenyl, alkoxy, or amino(lower alkyl);
$R^{10}$ is hydrogen, aryl, cycloalkyl, or cycloalkenyl, wherein the aryl, cycloalkyl or cycloalkenyl group may be substituted with 1 to 5 substituents selected from 1 to 5 halo, 1 to 3 nitro, 1 to 3 cyano, 1 to 3 sulfhydryl, 1 to 3 sulfinyl, 1 to 3 sulfonyl, 1 to 3 sulfoxyl, 1 to 3 hydroxyl, 1 to 3 carboxyl, 1 to 3 haloalkyl,

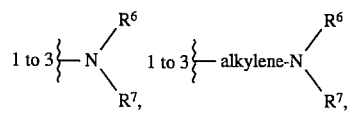

and, for cycloalkyl and cycloalkenyl only, 1 to 2 oxo.

DETAILED DESCRIPTION OF THE INVENTION

Definition of Terms

Listed below are definitions of various terms used to describe this invention. These definitions apply to the terms as used throughout this specification, unless otherwise limited in specific instances, either individually or as part of a larger group.

The terms "alkyl", "alk-" and "alkoxy" refer to straight or branched chain hydrocarbon groups having 1 to 12 carbon atoms. The terms "lower alkyl" and "lower alkoxy" refer to groups of 1 to 4 carbon atoms, which are preferred.

The term "aryl" or "ar-" refers to phenyl, naphthyl, and biphenyl.

The term "alkenyl" refers to straight or branched chain hydrocarbon groups of 2 to 10 carbon atoms having at least one double bond, preferably 1,2, or 3 double bonds. Groups of two to four carbon atoms are preferred.

The term "alkynyl" refers to straight or branched chain groups of 2 to 10 carbon atoms having at least one triple bond, preferably 1, 2, or 3 triple bonds. Groups of two to four carbon atoms are preferred.

The term "alkylene" refers to a straight chain bridge of 1 to 5 carbon atoms that is attached by single bonds (e.g., —$(CH_2)m$-wherein m is 1 to 5), which may be substituted with 1 to 3 lower alkyl groups.

The term "alkenylene" refers to a straight chain bridge of 1 to 5 carbon atoms having one or two double bonds and which is attached by single bonds (e.g., —CH=$CH_2$—CH= CH—, —$CH_2$—CH=CH-or —$CH_2$—CH=CH—$CH_2$—) which may be substituted with 1 to 3 lower alkyl groups.

The terms "cycloalkyl" and "cycloalkenyl" refers to cyclic hydrocarbon groups of 3 to 8 carbon atoms.

The terms "halogen" and "halo" refers to fluorine, chlorine, bromine and iodine.

The term "natural amino acid residue" refers to glycyl and the L-form of alanyl, arginyl, asparaginyl, aspartyl, cysteinyl, glutamyl, glutaminyl, histidyl, isoleucyl, leucyl, lysyl, methionyl, phenylalanyl, prolyl, seryl, threonyl, tryptophyl, tyrosyl, and valyl.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

Preferred Moieties

The following moieties are preferred for the polypeptide of formula I:

$A^1$ through $A^{12}$ are as defined above, with none replaced by any other natural amino acid residue;

$A^{12}$'s aromatic ring is substituted with one iodo atom, with a $^{125}I$ atom most preferred;

$A^{13}$ is alanyl;

AA is a single bond or L-glycyl-L-asparaginyl-L-glutamyl-L-glutaminyl, wherein the glycyl residue is attached to $R^1$; and $R^1$ is hydrogen or —$R^9$—$R^{10}$ wherein $R^{10}$ is hydroxyphenyl (para-hydroxyphenyl most preferred);

$R^2$ is hydrogen.

Use and Utility

Polypeptides defined by formula I have several advantages over known MHC Class I-derived polypeptides, including increased potency, stability in bioassay buffers, capability for radioiodination with retention of activity, and avoidance of aggregation or gel formation.

The polypeptides defined by formula I may be used in methods for enhancing or reducing the physiological response of a cell as a result of binding to certain cellular components. Such cellular components may be receptors, such as the insulin receptor, adrenergic receptors ($\alpha 1$, $\alpha 2$, $\beta 1$, $\beta 2$, and $\beta 3$), insulin-like growth factor I (IGFI) receptor, IGFI receptor, transferrin, T-cell receptor, low density lipid (LDL) receptor, and the like. Such cellular components may also be transporters, such as glucose transport proteins (e.g., GLUT-4); receptor-bound ligands, such as insulin; or other membrane-bound components, such as epidermal growth factor precursor protein or the native MHC Class I antigen protein. For example, the polypeptides may be used to enhance glucose uptake in a mammalian cell by combining the cell with either the polypeptide or a composition of matter in which the polypeptide is covalently bound to insulin or a functional segment thereof (i.e., a segment that binds to the insulin receptor as an agonist.)

For therapeutic uses, the polypeptide may be employed in a variety of ways. In particular, it may be administered orally or parenterally (e.g., subcutaneously, intraperitoneally, intravascularly). Formulations of the polypeptide will usually involve a physiologically acceptable medium, such as deionized water, saline, aqueous ethanol, phosphate buffered saline (PBS), and the like. Other additives may be included, such as buffers, stabilizers, other proteins, bacteriocides, and the like. The manner of formulation will vary depending upon the mode of administration (e.g., transdermal patch), the intended treatment (e.g., alleviation of diabetes mellitus), and the like. The formulation may involve pills, capsules, liposomes, time-released coatings, degradation-inhibiting coatings, and the like.

The polypeptide defined by formula I may also be used diagnostically, as a ligand to determine the presence of such cellular components as those described above. A cell suspected of containing such a cellular component would be combined with the polypeptide, alone or covalently bound to a ligand of interest (e.g., insulin) or a functional segment. Cells could be screened in vivo or in vitro, intact or as a lysate. Cells could be obtained from blood, biopsies, and the like. A number of protocols for such screening assays are known; for example, ELISA, EMIT, SLFIA, RIA, CEDIA, and the like.

Various means of determining the presence of a complex with the cellular component may be used. For example, a tryptophyl or para-nitrophenylalanyl residue of the polypeptide could be detected by spectrophotometry. Alternatively, the polypeptide could be directly or indirectly labeled with a detectable signal, such as a radioisotope or fluorescent moiety. In one preferred embodiment, the polypeptide of formula I includes a radioactive iodo atom ($^{125}I$) at $A^{12}$. By thus tracing the polypeptide, cells could be diagnosed for the presence of cellular components that bind the polypeptide or MHC Class I antigen.

In addition, the binding pattern of cellular membrane components on the surface of various cells with MHC Class I antigen can be determined using the foregoing procedures. Disease states resulting from inappropriate (either increased or decreased) complexation between MHC Class I antigens and receptors can be determined.

A polypeptide defined by formula I may also be used in a competitive binding assay to identify enhancers or inhibitors of cellular components that bind the polypeptide. In such an assay, a test compound competes with the polypeptide for binding to a cellular component. The presence of a complex between the cellular component and the polypeptide may be detected by spectrophotometry, radioactivity, or fluorescence as described above. For example, GLUT4 glucose transporters in whole cells or in a lysate are treated with the polypeptide and a test compound. To enable detection of a complex between the polypeptide and the cellular component, the polypeptide includes $^{125}$I at $A^{12}$. Radioactivity detection will identify which test compounds outcompete the polypeptide for binding to GLUT4 glucose transporters.

Process of Preparation

The peptides defined by formula I may be prepared by the following exemplary process.

A resin-coupled carboxyl terminal residue I
$P^1$-$A^{13}$-$P^2$-resin
is treated with a deprotecting agent (e.g., piperidine) in an organic solvent or solvent mixture such as dimethylformamide (DMF) and toluene. The resulting deprotected compound is coupled with the N-α-protected amino acid II
$p^1$-$A^{12}$-OH
in the presence of a coupling reagent such as benzotriazole-1-yloxytris(dimethylamino)phosphonium hexafluorophosphate (BOP) and 1-hydroxybenzotdazole (HOBt)in an organic solvent or solvent mixture (e.g., DMF/methylene chloride) at about 20° to 30° C. in a molar ratio of about 1:4 compound I:II to form a resin-coupled dipeptide III
$p^1$-$A^{12}$-$A^{13}$-$p^2$-resin.
In compounds I to III and throughout this specification, $P^1$ is an amino-protecting group such as fluorenylmethoxycarbonyl (Fmoc) and $P^2$ is a para-alkoxybenzyl ester linkage. The reaction may be effected with an automated peptide synthesizer (e.g., Milligen Biosearch 9600).

The foregoing procedure for peptide III is repeated with other nitrogen-protected amino acids until all residues of formula I have been coupled to the resin. Sidechain-protecting groups may be used in this process for sidechains having reactive functionalities, such as hydroxyl, carboxyl, amino, mercapto, guanidino, imidazolyl, indolyl and the like. The particular protecting groups used for any amino acid residues depend upon the sidechains to be protected and are generally known in the art. Exemplary sidechain protecting groups are t-butyl, benzyl, benzoyl, acetyl, halocarbobenzoxy, and the like for hydroxyl; cyclohexyl, benzyl, methyl, ethyl, t-butyl and the like for carboxyl; benzyl, 4-methylbenzyl, 4-methoxybenzyl, acetyl, acetamidomethyl, trimethylphenyl (trityl) and the like for mercapto; t-butyloxycarbonyl (BOC), carbobenzoxy (Cbz), halocarbobenzoxy, 9-fluorenylmethoxycarbonyl (Fmoc), phthaloyl (Pht), p-toluenesulfonyl (Tos), trifluoroacetyl, 2-(trimethylsilyl)ethoxycarbonyl (TEOC), and the like for amino; 2,4-dinitrophenyl, benzyloxymethyl, Tos, BOC, tdtyl and the like for imidazolyl; Cbz, TEOC, 2,2,2-trichloroethyl carbamate (TROC), formyl and the like for indolyl; and 2,2,5,7,8-pentamethylchroman-6-sulfonyl (PMC), 4-methoxy-2,3, 6-trimethylbenzenesulfonyl (MTR), Tos, nitro, bis (1-adamantyloxycarbonyl) and the like for guanidino.

Sidechain protecting groups may be removed, if desired, by treatment with one or more deprotecting agents in an inert solvent or solvent mixture (e.g., dimethylformamide, methylene chloride). Suitable deprotecting agents are generally known in the art. Exemplary deprotecting agents are thiophenol, mercaptoethanol and the like for removing 2,4-dinitrophenyl; trifluoroacetic acid (TFA) and the like for butoxycarbonyl; hydrofluoric acid, trifluoromethanesulfonic acid and the like for several different protecting groups. For further examples of protecting groups and suitable deprotecting agents, see Bodansky M. and Bodansky, A., *The Practice of Peptide Synthesis*, Springer-Verlag, Inc. (1984); and Greene, T. W. and Wuts, P., *Protective Groups in Organic Synthesis* (2d ed.), John Wiley & Sons, Inc. (1991).

The fully formed polypeptide may be cleaved from the resin by methods generally known in the art. For example, the resin-bound polypeptide may be treated with an acid, such as trifluoroacetic acid (TFA), hydrofluoric acid, trifluoromethanesulfonic acid, and the like. In one embodiment, the resin-bound peptide may be treated with an acid-alcohol-solvent mixture (e.g., trifluoroacetic acid/phenol/water/thioanisole/ethanedithiol) to yield a polypeptide of formula I.

The complete polypeptide defined by formula I can be covalently bound to insulin or a functional segment thereof by methods generally known in the art.

The invention will now be further described by the following working example, which is a preferred embodiment of the invention. This example is illustrative rather than limiting. Unless otherwise indicated, all temperatures are in degrees Celsius (°C.).

EXAMPLE 1 (SEQ. ID. NO.:1)

Glycyl-L-asparaginyl-L-α-glutamyl-Lglutaminyl-L-seryl-L-phenylalanyl-L-arginyl-L-valyl-L-α-aspartyl-L-leucyl-L-arginyl-L-threonyl-L -leucyl-L-arginyl-L-tyrosyl-L-alanine.

A. SEQ. ID. No.: 2

Glycyl-L-asparaglynyl-0-(1,1-dimethylethyl)-L-α-glutamyl-L-glutaminyl-S-(1,1-dimethylethyl)-L-seryl-L-phenylalanyl-N-(Pmc)-L-arginyl-L-valyl-0-(1,1-dimethylethyl)-L-α-aspartyl-L-leucyl-N-(Pmc)-L-arginyl-0-[(1,1-dimethylethyl)carbonyl]-L-threonyl-L-leucyl-L-leucyl-N-(Pmc)-L-arginyl-0-(1,1-dimethylethyl)-L-tyrosyl-L-alanine, [4-[(4-resinphenyl)methoxy]phenyl]methyl ester.

Protected polypeptide intermediate A was assembled stepwise by the solid phase method on a Milligen Biosearch Model 9600 Peptide Synthesizer using the Fmoc/BOP chemistry program supplied with the instrument. The starting p-alkoxybenzyl alcohol (Wang) resin (polystyrene, 1% divinylbenzene copolymer), loaded with the C-terminal Fmoc-alanine (0.377 g, 0.20 mmol), was purchased from Bachem California. (The formal name for this compound is N-[(9H-fluoren-9-ylmethoxy)carbonyl]-L-alanine, [4[(4-resinphenyl)methoxy]phenyl]methyl ester.) Amino acids were coupled as their N-α-Fmoc derivatives. The reactive sidechains of tyrosine, aspartic acid, threonine, and serine were protected with t-butyl; the guanidinium group of arginine with PMC. Fmoc groups were removed at each cycle by a 10-minute treatment with 30% piperidine/35% DMF/35% toluene. Each amino acid derivative was coupled for one hour at room temperature in four-fold molar excess, using one equivalent of BOP and HOBt in 1:1 v/v DMF/methylene chloride. Fmoc-asparagine and Fmoc-glutamine were coupled as their pentafluorophenyl esters (Bachem Bioscience, Philadelphia, Pa.). After the final coupling, the N-terminal Fmoc group was removed as described above. The dried, protected polypeptidyl resin A weighed 0.977 g. Weight gain: 98% of theory.

B. SEQ. ID. NO.:1

Glycyl-L-asparaginyl-L-α-glutamyl-Lglutaminyl-L-seryl-L-phenylalanyl-L-arginyl-L-valyl-L-α-aspartyl-L-leucyl-L-arginyl-L-thereonyl-L-leucyl-L-leucyl-L-arginyl-L-tyrosyl-L-alanine.

Simultaneous deprotection and cleavage of the polypeptide from the resin was accomplished by stirring the protected polypeptidyl resin (0.50 g, 0.102 mmol) in 10 mL of trifluoroacetic acid/phenol/water/thioanisole/ethanedithiol (10:0.75:0.5: 0.5: 0.25) for 1.5 hours at room temperature. The resin was removed by filtration, and the filtrate was concentrated in vacuo. The crude product was precipitated with methyl t-butyl ether (MTBE), filtered and washed with MTBE, then redissolved in 50% aqueous acetic acid. The solution was diluted with water and lyophilized. Yield: 385 mg (greater than 100% of theory).

Four sample aliquots (20 mg each) were injected into a Vydac $C_{18}$ column (22×250 mm, 10 μ, 300 Å) and reversed-phase HPLC was performed under the following conditions:
Solvent A—0.1% TFA in water;
Solvent B—0.1% TFA in acetonitrile;
linear gradient—28–32% B in A over 50 minutes;
flow rate—8 mL/minute.

Fractions containing the major peak (215 nm), eluting at 27.85 minutes, were pooled and lyophilized to yield 34.3 mg (43%) of Example 1 as a white powder.

Analytical HPLC of Example 1: Vydac $C_{18}$ (4.6×250 nm); 215 nm, 1.0 mL/minute: 1) linear gradient from 5% to 55% B in A over 50 minutes; retention time 34.61 minutes. Purity: greater than 98%; (Solvent A, 0.1% trifluoroacetic acid in water; Solvent B, 0.1% trifluoroacetic acid in acetonitrile).

EXAMPLES 2 and 3 (SEQ. ID. NOS.:3 and 4)

Glycyl-L-asparaginyl-L-α-glutamyl-L-glutaminyl-L-seryl-L-phenylalanyl-L-arginyl-L-valyl-L-α-aspartyl-L-leucyl-L-arginyl-L-threonyl-L-leucyl-L-leucyl-arginyl-4-hydroxy-3-iodo-L-phenylalanyl-L-alanine; and Glycyl-L-asparaginyl-L-α-glutamyl-L-glutaminyl-L-seryl-L-phenylalanyl-L-arginyl-L-valyl-L-α-aspartyl-L-leucyl-L-arginyl-L-threonyl-L-leucyl-L-leucyl-arginyl-4-hydroxy-3,5-diiodo-L-phenylalanyl-L-alanine.

To a stirred solution of Example 1 (4.3 mg, 1.72 μmol) in water (4.3 mL) were successively added, at room temperature, phosphate buffer (pH 7.4, 8.6 mL), sodium iodide (1.90 μmol, 0.95 mL of a 2.0 mM solution in the same phosphate buffer) and chloramine-T (1.90 μmol, 0.95 mL of a 2.0 mM solution in the same phosphate buffer). After 1 hour, the reaction was quenched by the addition of 1 M sodium metabisulfate (0.1 mL); the resulting solution was lyophilized to a solid. This solid was dissolved in 0.1% aqueous trifluoroacetic acid (3 mL) and the solution was loaded onto a MegaBond Elut™ C18 cartridge. Elution with 0.1% aqueous triflaoroacetic acid (8.0 mL) was followed by 25% acetic acid (20 mL). Fraction 3 (8–28 mL) afforded, after lyophilization, 4.0 mg of a mixture of Example 1 (52%, FAB-MS: (M+H)+ 2038.1 ), mono-iodinated product (Example 2; 7%, FAB-MS: (M+H)+2164.0) and diiodinated product (Example 3; 41%, FAB-MS: (M+H)+2290.0). Quantitation of product distribution was performed by peak integration of the three components separated by analytical HPLC under the following conditions: Vydac C18 column (4.6×250 mm, 5 μM, 300 A), 215/275 nm, 1.0 mL/min; linear gradient from 25% to 40% B in A over 60 minutes (A: 0.1% trifluoroacetic acid in water; B: 0.1% trifluoroacetic acid in acetonitrile); Example 1, retention time, 26 minutes; monoiodinated Example 2, retention time, 33 minutes; Example 3, retention time, 39 minutes.

The mixture of Examples 1, 2, and 3 were subjected again to iodination as described above, except that 2.65 μmol of sodium iodide and chloramine-T were used, to yield Example 3 quantitatively. Example 3 was injected into a Vydac $C_{18}$ column (22×250 mm, 10 μ, 300 A), and reverse phase HPLC was performed under the following conditions: Solvents A and B: same as above; linear gradient from 30% to 35% B in A over 50 minutes; flow rate: 8 mL/min. The fractions containing the major peak (215 nm) eluting at 46.43 minutes were pooled and lyophilized to yield 2.5 mg (53%, from Example 1 ) of Example 3 as a white, fluffy powder.

Analytical HPLC of Example 3: Vydac $C_{18}$ (4.6×250 mm); 215 nm, 1.0 mL/min: linear gradient from 28% to 38% B in A over 40 minutes; room temperature, 28.18 minutes. Purity: greater than 98%; (Solvents A and B, same as above)

---

What is claimed is:

1. A compound of the formula

[H—AA—$A^1$—$A^2$—$A^3$—$A^4$—$A^5$—$A^6$—$A^7$—$A^8$—$A^9$—$A^{10}$—$A^{11}$—$A^{12}$—$A^{13}$—H] H—AA—$A^1$—$A^2$—$A^3$—$A^4$—$A^5$—$A^6$—$A^7$—$A^8$—$A^9$—$A^{10}$—$A^{11}$—$A^{12}$—$A^{13}$—OH wherein:

AA is a single bond or a polypeptide chain of 1 to 12 natural amino acid residues:

$A^1$ is seryl;

$A^2$ is phenylalanyl;

$A^3$ is arginyl;

$A^4$ is valyl;

$A^5$ is aspartyl;

$A^6$ is leucyl;

$A^7$ is arginyl;

$A^8$ is threonyl;

$A^9$ is leucyl;

$A^{10}$ is leucyl;

$A^{11}$ is arginyl; and $A^{12}$ is tyrosyl;

wherein one of $A^1$ through $A^{12}$ may be replaced with a natural amino acid residue;

wherein when $A^{12}$ is phenylalanyl, tyrosyl or tryptophyl, its aromatic ring may be substituted with 1 or 2 radioiodine atoms;

$A^{13}$ is a natural amino acid residue other than tyrosyl, phenylalanyl, histidyl or tryptophyl, the D-form of a natural amino acid residue other than tyrosyl, phenylalanyl, histidyl, or tryptophyl,

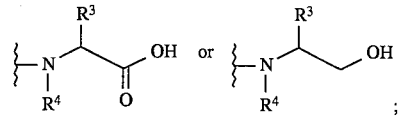

$R^3$ is hydrogen, —$R^9$—$R^{10}$, or

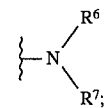

$R^4$ is hydrogen or alkyl, or $R^3$ and $R^4$ together are alkylene;

R6 and $R^7$ are each independently hydrogen, alkyl, cycloalkyl, or cycloalkylalkyl, or together are alkylene or alkenylene;

$R^9$ is a single bond, alkyl, alkenyl, alkoxy, or amino(lower alkyl);

$R^{10}$ is hydrogen, cycloalkyl, or cycloalkenyl, wherein the cycloalkyl or cydoalkenyl group may be substituted with 1 to 5 substituents selected from a group consisting of 1 to 5 halo, 1 to 3 nitro, 1 to 3 cyano, 1 to 3 sulfhydryl, 1 to 3 sulfinyl, 1 to 3 sulfonyl, 1 to 3 sulfoxyl, 1 to 3 hydroxyl, 1 to 3 carboxyl, 1 to 3 haloalkyl,

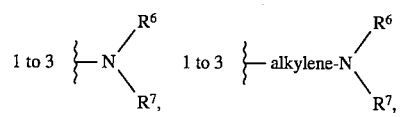

and 1 to 2 oxo.

2. The compound of claim 1, wherein none of $A^1$ through $A^{12}$ is replaced by any other natural amino acid residue.

3. The compound of claim 1, wherein $A^{13}$ is alanyl.

4. The compound of claim 1, wherein AA is a single bond or L-glycyl-L-asparaginyl-L-glutamyl-L-glutaminyl, wherein the glycyl residue is attached to $R^1$.

5. The compound of claim 1, wherein $A^{12}$ is phenylalanyl, tyrosyl or tryptophyl.

6. The compound of claim 5, wherein the aromatic ring of $A^{12}$ is substituted with one iodo atom.

7. The compound of claim 5 wherein the iodo atom is a $^{125}I$ atom.

8. A method for detecting the presence of an MHC Class I antigen-dependent receptor in a cell, which comprises:

(a) combining the cell suspected of containing said receptor with a composition of matter of claim 6, and (b) determining the presence of a complex between the composition of matter of claim 6 and the receptor as an indication of the presence of an MHC Class I antigen-dependent receptor in the cell.

9. A composition of matter comprising:

(a) a compound of claim 1, covalently bound to (b) insulin or a functional segment thereof.

10. A method for detecting the presence of an MHC Class I antigen-dependent receptor in a cell, which comprises:

(a) combining the cell suspected of containing said receptor with a compound of claim 1, and (b) determining the presence of a complex between the compound of claim 1 and the receptor as an indication of the presence of an MHC Class I antigen-dependent receptor in the cell.

11. A method for screening for compounds that bind to the insulin receptor, which comprises:

(a) treating an insulin receptor with a compound of claim 1 and a test compound;

(b) analyzing the insulin receptor to determine whether the test compound outcompetes the compound of claim 1 for binding to the insulin receptor.

12. The method of claim 11, wherein the compound has a radioactive iodo atom at $A^{12}$ and the analyzing step is carried out by measuring the radioactivity emanating from the compound.

13. The compound of claim 1 selected from the group consisting of compounds defined by SEQ. ID. NOS.: 1, 3, and 4.

* * * * *